(12) United States Patent
Girch, Jr. et al.

(10) Patent No.: US 8,040,066 B1
(45) Date of Patent: Oct. 18, 2011

(54) FLESH ILLUMINATING DEVICE

(76) Inventors: James J. Girch, Jr., Arleta, CA (US);
Terri R. Smith, Simi Valley, CA (US);
Eric J. Allard, Woodland Hills, CA (US)

( * ) Notice: Subject to any disclaimer, the term of this patent is extended or adjusted under 35 U.S.C. 154(b) by 319 days.

(21) Appl. No.: 12/383,806

(22) Filed: Mar. 30, 2009

(51) Int. Cl.
*H01J 7/44* (2006.01)

(52) U.S. Cl. .......................................... 315/33; 315/313

(58) Field of Classification Search .................... 315/33, 315/35, 312, 313
See application file for complete search history.

(56) References Cited

U.S. PATENT DOCUMENTS

| | | | |
|---|---|---|---|
| 4,930,143 A | 5/1990 | Lundgren et al. | |
| 6,955,444 B2 * | 10/2005 | Gupta | 362/105 |
| 7,001,056 B2 | 2/2006 | Clegg | |
| 7,239,909 B2 * | 7/2007 | Zeman | 600/473 |
| 7,345,418 B2 * | 3/2008 | Nagatomi et al. | 313/503 |
| 7,364,315 B2 | 4/2008 | Chien | |
| 7,386,336 B2 * | 6/2008 | Fine et al. | 600/335 |
| 7,621,638 B2 * | 11/2009 | Su et al. | 351/221 |

\* cited by examiner

*Primary Examiner* — Don Le
(74) *Attorney, Agent, or Firm* — Albert O. Cota

(57) ABSTRACT

A flesh illuminating device (FID) (10) that is comprised of three major elements: an electronic control unit (ECU) (12), an LED assembly (50) and a flesh attachment assembly (70). The ECU (12) and the LED assembly (50) are attached to the flesh attachment assembly (70) which is dimensioned to allow the LED assembly (50) to be attached to a selectable section of flesh. The section of flesh can consist of either an arm, a hand, a leg, a foot, at least one ear lobe or at least one breast. When the FID (10) is manually or remotely turned ON, the LED assembly (50) which preferably consists of at least one LED (60), illuminates causing the selected section of flesh to illuminate.

14 Claims, 4 Drawing Sheets

FLESH ILLUMINATING DEVICE

TECHNICAL FIELD

The invention pertains generally to light illuminating devices, and more particularly to a flesh illuminating device that is comprised of a light source such as LEDs which are positioned to interface with a selected section of flesh. When the LEDs are energized by a power source the flesh illuminates.

BACKGROUND ART

A search of the prior art did not disclose any literature or patents that read directly on the claims of the instant invention. However, the following U.S. patents are considered related.

| PAT. NO.  | INVENTOR      | ISSUED       |
|-----------|---------------|--------------|
| 4,930,143 | Lundgren et al | 29 May 1990  |
| 7,001,056 | Clegg         | 21 Feb. 2006 |
| 7,364,315 | Chien         | 29 Apr. 2008 |

The 4,930,143 patent discloses a method and apparatus for stereotactic localization of cancer suspect lesions of a female breast in connection with X-ray mammography. "The lesion is imaged in two directions, and the position of the lesions is calculated from the parallax displacement between the two images. The X-ray tube and the film are held stationary, and the parallax displacement is effected by moving the breast laterally.

The 7,001,056 patent discloses an LED illuminated pendant formed of strands having a pair of electrical wires of positive and negative polarity. A barrel, a printed circuit board and the pendant which is lit by an LED, are mounted on the pendant. The barrel houses a battery cage that holds a plurality of batteries that power the pendant.

The 7,364,315 patent discloses a tubular electro-luminescent light device that illuminates a panel incorporated with an inverter. The panel has a much narrower width than a tube means containing the panel which allows the panel to bend in any direction and angle within the tube to provide desired light effects.

DISCLOSURE OF THE INVENTION

The flesh illuminating device (FID) includes a light source such as an LED assembly that is designed to interface with a section of human flesh. When power is applied to the FID, the LED assembly illuminates causing the flesh to illuminate in accordance with a selectable lighting sequence. In its basic design configuration the FID is comprised of a) a power source,
b) at least one light source having means for interfacing with the section of human flesh,
c) an electrical power switch that is connected between the power source and the at least one light source. When the power switch is placed in the ON position, the power source illuminates the at least one light source causing the flesh to illuminate.

The flesh is selected from the group consisting of an arm, a hand, a leg, a foot, at least one ear lobe and at least one breast. The power source is comprised of a battery that preferably consists of a rechargeable battery. The light source is selected from the group consisting of a single light emitting diode (LED), a cluster of LEDs, an incandescent light and an electroluminescent panel (ELP). Preferably, the LEDs are comprised of super-bright LEDs that are selected to provide either a red, white, blue, yellow or green color.

In view of the above disclosure, the primary object of the invention is to produce an FID that is safely and easily attached to a section of a selectable human flesh. When the FID produces a light source the section of flesh illuminates.

In addition to the primary object of the invention it is also an object of the invention to produce an FID that:

can be designed to be operated manually or remotely,
can be utilized to locate and view anomalies that are located within the flesh,
can be utilized with incandescent lights, ultraviolet lamps and infrared lamps,
is reliable and relatively maintenance free,
can be utilized by exotic dancers, other entertainers and the general public,
can be attached to a variety of structures applicable to the size and location of the flesh that is to be illuminated,
is easily removed from a garment when the garment requires laundering,
is cost effective from both a consumer's and manufacturer's point of view.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
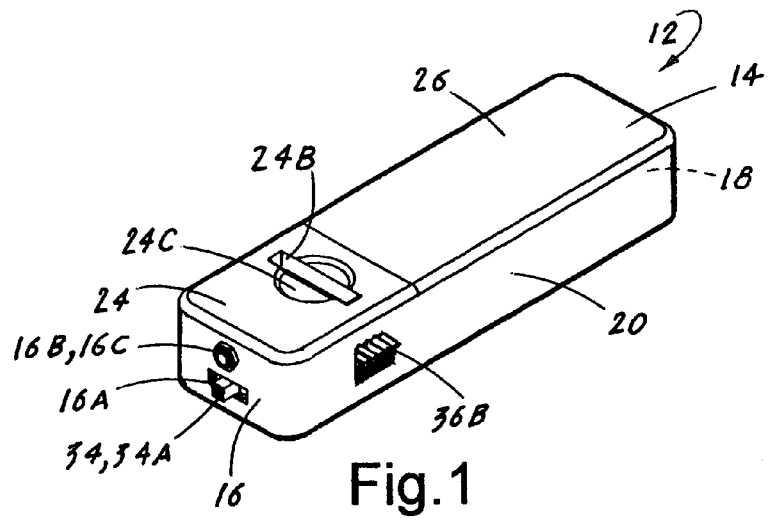
FIG. 1 is a perspective view of the electronic control unit (ECU).

The best mode for carrying out the invention is presented in terms of a preferred embodiment for a flesh illuminating device (FID) 10. The flesh is selected from the group consisting of an arm, a hand, a leg, a foot, at least one ear lobe and at least one breast. The FID 10, as shown in FIGS. 1-8, is comprised of the following three major elements: an electronic control unit (ECU) 12, at least one LED assembly 50 and a flesh attachment assembly 70.

The ECU 12, as shown in FIGS. 1-5, is comprised of an enclosure 14, an upper enclosure cover 23, a lower enclosure cover 28, a printed circuit board (PCB) 32, a light display card 40 and a pair of batteries 46.

Figure 5:
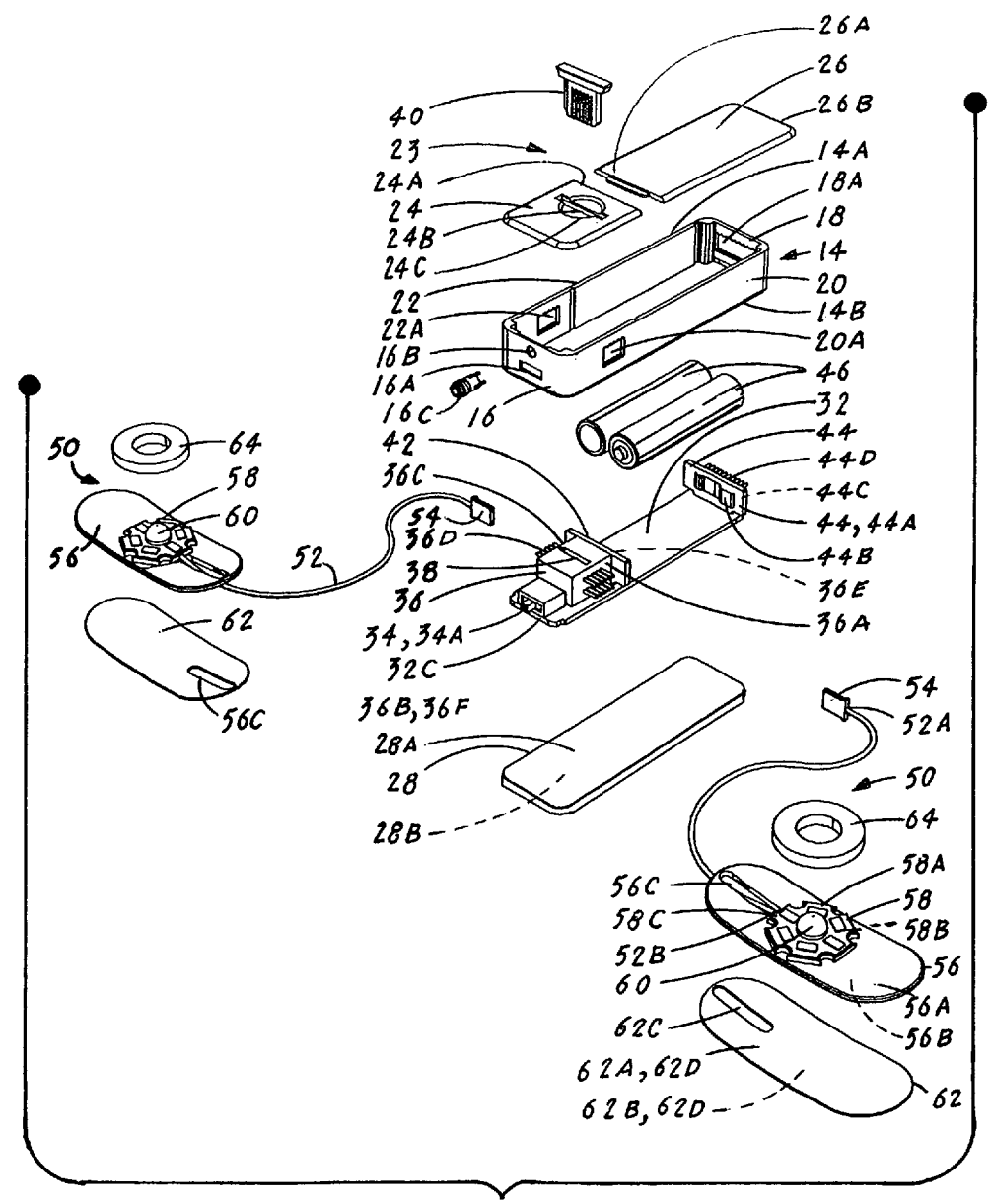
FIG. 5 is an exploded view of the ECU assembly and the LED assembly.

The enclosure 14 is comprised of an upper edge 14A, a lower edge 14B, and a front section 16 having a switch slot 16A and a battery charging jack bore 16B. Into the bore 16B is attached a battery charging jack 16C, as shown in FIG. 5. The enclosure 14 also includes a front section 16, rear section 18 having a rear LED receptacle opening 18A, an integral right side 20 having a right LED receptacle opening 20A, and an integral left side 22 having a left LED receptacle opening 22A.

The second major element comprising the FID 10 is a light source that preferably consists of at least one LED assembly 50, as shown in FIG. 5. The assembly 50 is comprised of an electrical cable 52 having a first end 52A and a second end 52B. To the first end 52A is connected an LED jack 54 that is configured to fit into an LED receptacle 36B,36D,44D. The LED assembly 50, which consists of at least one LED 60, also includes an LED heat sink 56, an LED mounting structure 58 and an LED assembly attachment member 62. The LEDs 60 are preferably super bright LEDs 60 that can consist of a single LED 60 or a cluster of LEDs 60. The LEDs can be selected to emit either a red, white, blue, yellow or green color.

The LED heat sink 56 has an upper surface 56A, a lower surface 56B and a cable guide slot 56C. The LED mounting structure 58 has an upper surface 58A, a lower surface 58B and a cable attachment pin 58C to which is attached the second end 52B of the electrical cable 52, as shown in FIG. 5. The lower surface 58B is attached to the upper surface 56A of the LED heat sink 56, and the upper surface 56A is attached to at least one LED 60 that is connected to the second end 52B of the electrical cable 52.

The LED assembly attachment member 62 has an upper surface 62A, a lower surface 62B and a cable guide slot 62C that is in alignment with the cable guide slot 56A located on the LED heat sink 56. The upper surface 62A of the member 62 is attached by an attachment means 62D to the lower surface 56B of the LED heat sink 56. The lower surface 62B of the member 62 is also attached by the attachment means 62D to the upper surface 62A of the PCB 32. To prevent the emission of sidelight, and to prevent the flesh from the heat emitted from the LEDs, an LED light-leak and thermal insulating gasket 64 is placed over the sides of the LEDs 60.

Figure 2:
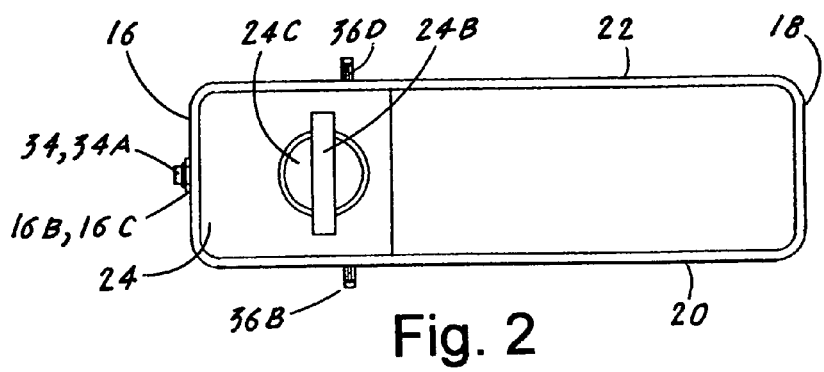
FIG. 2 is a top plan view of the ECU.
Figures 3, 4:
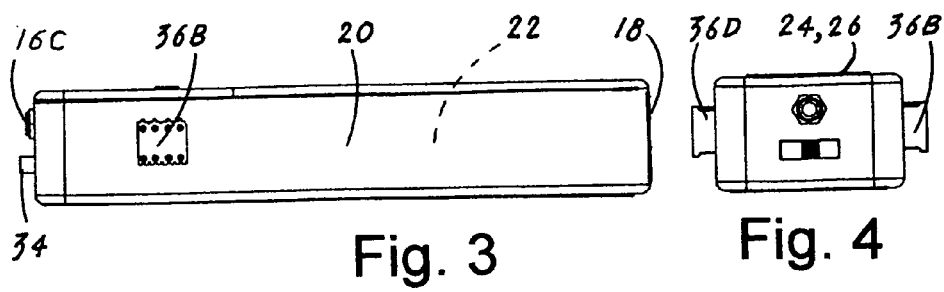
FIG. 3 is a side elevational view of the ECU.
FIG. 4 is a front elevational view of the ECU.

The upper enclosure cover 23 is comprised of a fixed cover 24 and a removeable battery cover 26. The fixed cover 24 is preferably attached by a mechanical means 30, to the upper edge 14A of the enclosure 14. The fixed cover 24 extends partially inward from the enclosure's front section 16 and terminates with an inner edge 24A, as shown in FIGS. 1, 2 and 5. The fixed cover 24 also includes a light display card slot 24B that preferably is surrounded by a finger gripping indentation 24C which allows the card to be easily grasped. The battery cover 26, as also shown in FIGS. 1, 2 and 5, is dimensioned to fit over the upper edge 14A of the enclosure 14 and has a front edge 26A and a rear edge 26B. The front edge 26A is removably attached to the inner edge 24A of the fixed cover 24. The rear edge 26B terminates over the rear section 18 of the enclosure 14. The lower enclosure cover 28, as shown in FIG. 5, has an inner surface 28A and an outer surface 28B. The cover 28 is dimensioned to be rigidly attached by the mechanical means 30 or optionally by an adhesive to the lower edge 14B of the enclosure 14.

The printed circuit board (PCB) 32, as shown in FIG. 5, has an upper surface 32A, a lower surface 32B, a front edge 32C and a rear edge 32D. The PCB 32 is dimensioned to fit into the enclosure 14, with the lower surface 32B of the PCB 32 interfacing with the inner surface 28A of the lower enclosure cover 28. The PCB 32 has attached, as also shown in FIG. 5, a power switch 34, an FID control circuit 36, a front battery terminal 42 and an upward-extending rear section 44.

The power switch 34 in a preferred design consists of an accessible slide switch that is configured as a center OFF single-pole, double-throw switch that includes a switch control stem 34A. The switch 34 is attached adjacent to the front edge 32C of the PCB 32 with the switch control stem 34A protruding through the switch slot 16A located on the front section 16 of the enclosure 14.

The FID control circuit 36, which can be comprised of a microcontroller that is electronically connected to the power switch 34, via the PCB 32. The circuit 36 has a light display card slot 38, a right side 36A that includes at least one right LED connecting receptacle 36B and a left side 36C that includes at least one left LED connecting receptacle 36D. The circuit 36 is designed to operate in combination with the light display card 40 that is inserted into the light display card slot 38 via the light display card slot 24B located on the fixed cover 24. The light display card 40 has a programmed means for causing the FID control circuit 36 to control the lighting sequence of the LEDs 60. The LED lighting sequence can be selected to produce an illumination that is constant, blinks or moves sequentially in either a right direction or in a left direction or in other selectable lighting configurations.

Attached to the PCB 32 is a front battery terminal 42 and an upward-extending rear section 44. The section 44 has a front surface 44A and a rear surface 44C. From the front surface 44A extends a rear battery terminal 44B. From the rear surface 44C extends a rear LED receptacle 44D that is electrically connected via the PCB 32 to the FID control circuit 36.

Between the front battery terminal 42 and the rear battery terminal 44B are positioned the pair of batteries 46 which preferably are comprised of rechargeable batteries 48 that are recharged by inserting a battery charging unit (not shown) into the battery charging jack 16C located on the enclosure 14. The batteries 46 provide the electrical power source that is required to operate the FID 10 and to illuminate the LEDs.

The final element that comprises the FID 10 is the flesh attachment assembly 70 which can be configured as a strap 72 or as a brassiere 80.

Figure 6:
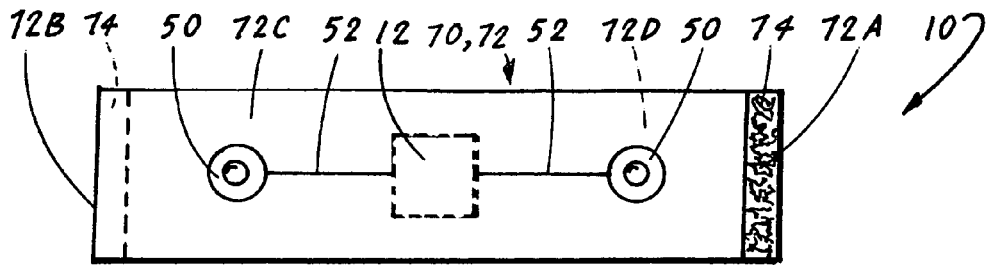
FIG. 6 is a top plan view of a strap having attached a flesh illuminating device (FID) attached thereto.

The strap 72, as shown in FIG. 6, has a first end 72A, a second end 72B, an inner surface 72C and an outer surface 72D. The LED assembly 50 is attached to the inner surface 72C of the strap 72 at a location that interfaces with a selected section of flesh. The ECU 12 is located on the outer surface 72D of the strap 70. The two ends 72A and 72B are preferably attached by means of a hook and loop fastener 74. When the LED assembly 50 is connected to the PCB 32 and the FID 10 is enabled by placing the power switch 34 in the ON position, the flesh that surrounds said LED assembly 50 will illuminate. The illumination will occur in accordance with the light sequence program that is stored in the light display card 40.

Figure 7:
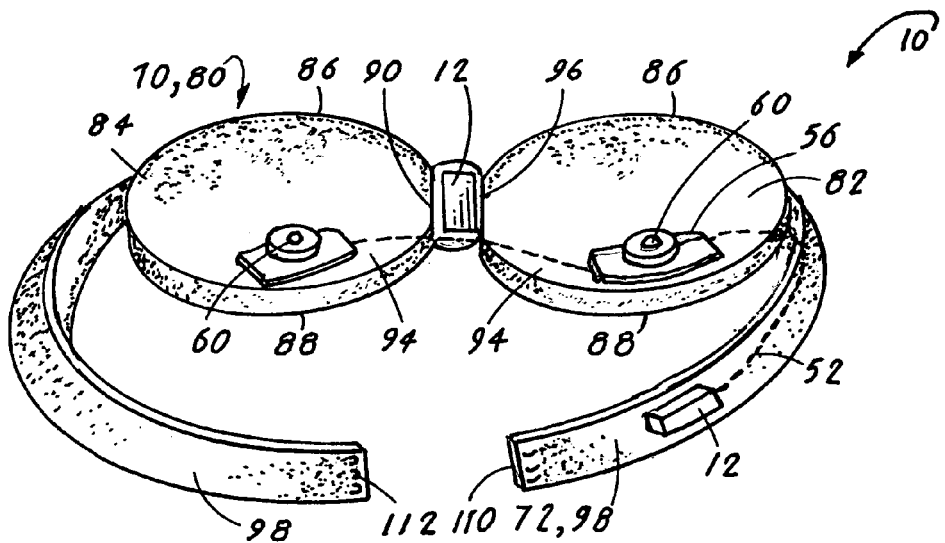
FIG. 7 is a perspective view of a brassiere having a FID attached thereto.

The brassiere 80, as shown in FIG. 7, is comprised of a right cup 82 and a left cup 84, wherein each cup has an upper edge 86, a lower edge 88, an inner edge 90, an outer edge 92 and an inner surface 94. The two cups 82,84 are joined at their inner edges 90 by a center section 96. The outer edge 92 of each cup has attached a body attachment strap 98, wherein each strap 98 has ends 110 that are placed around the body and are secured thereto typically by a clasp 112 or the like. An LED assembly 50 is attached by an attachment means, to the inner surface 94 and along the lower edge 88 of each cup 82,84.

The ECU 12, which controls the operation of the LED assembly 50, is attached to either the center section 96 of the brassiere 80 or to the outer surface 72D of one of the body attachment straps 98, as shown in FIG. 7. When the FID 10 is enabled by placing the power switch 34 in the ON position, the flesh that surrounds the LED assembly 50 will illuminate in accordance with the program that is stored in the light display card 40.

Figure 8:
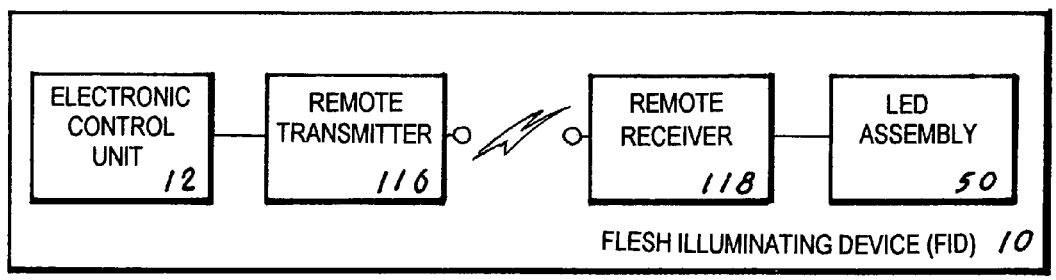
FIG. 8 is a block diagram of a FID that is operated remotely utilizing remote control technology.

To enhance the utility of the invention, the FID 10 can be designed to utilize a remote transmitter 116 and a remote receiver 118, as shown in FIG. 8. The transmitter 116 produces a radio frequency (RF) signal 120 that is received by the remote receiver 118 that is connected by electrical means to the FID 10.

While the invention has been described in detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

FLESH ILLUMINATING DEVICE
Element Designation (For convenience of the Examiner, not part of the specification)

| | | | |
|---|---|---|---|
| 10 | Flesh Illuminating Device (FID) | 30 | Attachment Means |
| 12 | Electronic Control Unit (ECU) | 32 | Printed Circuit Board (PCB) |
| 14 | Enclosure | 32A | Upper Surface |
| 14A | Upper Edge | 32B | Lower Surface |
| 14B | Lower Edge | 32C | Front Edge |
| 16 | Front Section | 32D | Rear Edge |
| 16A | Switch Slot | 32E | |
| 16B | Battery Charging Jack Bore | 32F | |
| 16C | Battery Charging Jack | 34 | Power Switch |
| 18 | Rear Section | 34A | Switch Control Stem |
| 18A | Rear LED Receptacle Opening | 34B | |
| 20 | Right Side | 36 | FID Control Circuit |
| 20A | Right LED Receptacle Opening | 36A | Right Side |
| 20B | | 36B | Right LED Receptacle |
| 22 | Left Side | 36C | Left Side |
| 22A | Left LED Receptacle Opening | 36D | Left LED Receptacle |
| 23 | Upper Enclosure Cover | 36E | Input |
| 24 | Fixed Cover | 36F | Output |
| 24A | Inner Edge | 36G | |
| 24B | Light Display Card Slot | 36H | |
| 24C | Finger Gripping Indentation | | |
| 26 | Battery Cover | 38 | Light Display Card Slot |
| 26A | Front Edge | 40 | Light Display Card |
| 26B | Rear Edge | 40A | |
| 28 | Lower Enclosure Cover | 42 | Front Battery Terminal |
| 28A | Inner Surface | 44 | Rear Section |
| 28B | Outer Surface | 44A | Front Surface |
| 28C | | 44B | Rear Battery Terminal |
| 28D | | 44C | Rear Surface |
| 44D | Rear LED Receptacle | 70 | Flesh Attachment Assembly |
| 44E | | 72 | Strap |
| 46 | Battery | 72A | First End |
| 48 | Rechargeable Battery | 72B | Second End |
| 50 | LED Assembly | 72C | Inner Surface |
| 52 | Electrical Cable | 72D | Outer Surface |
| 52A | First End | 74 | Hook and Loop Fastener |
| 52B | Second End | 76 | |
| 54 | LED Jack | 78 | |
| 56 | LED Heat Sink | 80 | Brassiere |
| 56A | Upper Surface | 82 | Right Cup |
| 56B | Lower Surface | 84 | Left Cup |
| 56C | Cable Guide Slot | 86 | Upper Edge |
| 58 | LED Mounting Structure | 88 | Lower Edge |
| 58A | Upper Surface | 90 | Inner Edge |
| 58B | Lower Surface | 92 | Outer Edge |
| 58C | Cable Attachment Pin | 94 | Inner Surface |
| 60 | LEDs | 96 | Center Section |
| 62 | Attachment Member | 98 | Body Attachment Strap |
| 62A | Upper Surface | 110 | Ends |
| 62B | Lower Surface | 112 | Clasp |
| 62C | Cable Guide Slot | 114 | |
| 62D | Attachment Means | 116 | Remote Transmitter |
| 62E | | 118 | Remote Receiver |
| 64 | LED Light-Leak and Thermal Insulating Gasket | 120 | Signal |
| 66 | | | |
| 68 | | | |

The invention claimed is:

1. A flesh illuminating device (FID) that functions in combination with at least one breast, said FID comprising:
 a) a rechargeable battery,
 b) a cluster of white light emitting diodes (LEDs) that interface with the at least one breast,
 c) an electrical power switch connected between said rechargeable battery and said cluster of white LEDs, wherein when said power switch is placed in an ON position, said cluster of white LEDs illuminate, thereby causing the at least one breast to illuminate, and
 d) a breast attachment means that is specifically designed to be attached to a selected section of the at least one breast that is to be illuminated.

2. A flesh illuminating device (FID) that functions in combination with a section of human flesh, said FID comprising:
 a) a power source,
 b) at least one light source having means for interfacing with the section of human flesh,
 c) an electrical power switch that is connected between said power source and said at least one light source, wherein when said power switch is placed on an ON position, said power source illuminates said at least one light source, thereby causing the flesh to illuminate, and
 d) a flesh attachment assembly that is designed to be attached to the selected section of the flesh that is to be illuminated.

3. A flesh illuminating device comprising:
 A. an electronics control unit (ECU) comprising:
  a) an enclosure having:
   (1) an upper edge and a lower edge,
   (2) a front section having a switch slot and a battery charging jack bore, wherein into the jack bore is inserted a battery charging jack,
   (3) a rear section having a rear LED receptacle opening,
   (4) an integral right side having a right LED receptacle opening, and
   (5) an integral left side having a left LED receptacle opening,
  b) an upper enclosure cover comprising:
   (1) a fixed cover that is attached by an attachment means to the upper edges of said enclosure and that extends partially inward from the front section of said enclosure and terminates with an inner edge, said fixed cover further having a light display card slot,
   (2) a removable battery cover that fits over the upper edge of said enclosure, said cover having a front edge that is removably attached to the inner edge of the fixed cover and a rear edge that terminates over the rear section of said enclosure,
  c) a lower enclosure cover having an inner surface, and an outer surface, wherein the cover is dimensioned to be rigidly attached by an attachment means to the lower edge of said enclosure,
  d) a printed circuit board (PCB) having an upper surface, a lower surface, a front edge and a rear edge, wherein said PCB is dimensioned to fit into said enclosure with the lower surface of said PCB interfacing with the inner surface of the lower enclosure cover, said PCB having attached:
   (1) a center OFF single-pole, double-throw power switch having a switch control stem, wherein said switch is attached adjacent the front edge of said PCB, with the switch control stem protruding through the switch slot located on the front section of said enclosure, wherein when said power switch is ON, said FID control circuit is enabled, thereby providing the means for controlling the operation of said FID,
(2) an FID control circuit that is electrically connected to said power switch via said PCB, said circuit having a light display card slot, a right side that includes a plurality of right LED connecting receptacle and a left side that includes a plurality of left LED connecting receptacles,
(3) a light display card that is inserted into the light display card slot via the light display card slot located on said fixed cover, wherein said light display card having means for causing said FID control circuit to control the lighting sequence of said LEDs,
(4) a front battery terminal,
(5) an upward-extending rear section having a front surface from where extends a rear battery terminal, and a rear surface from where extends a rear LED receptacle that is electrically connected via said PCB to said FID control circuit,
e) a battery that is positioned to make electrical contact respectively, with the front battery terminal and the rear battery terminal, wherein said battery provides the power to operate said FID,
B. at least one LED assembly comprising:
a) an electrical cable having a first end and a second end,
b) an LED jack connected to the first end of said electrical cable, wherein said LED jack is configured to fit into one of the LED receptacles,
c) an LED heat sink having an upper surface, a lower surface, and a cable guide slot,
d) an LED mounting structure having an upper surface and a lower surface, wherein the lower surface is attached to the upper surface of the LED heat sink, and to the upper surface is attached at least one LED that is connected to the second end of said electrical cable, and
e) an LED assembly attachment member having an upper surface, a lower surface and a cable guide slot that is in alignment with the cable guide slot located on the heat sink, wherein the upper surface of said member is attached by an attachment means to the lower surface of said heat sink and the lower surface of said member is attached by the attachment means to the upper surface of said PCB, and
C. a flesh attachment assembly configured as a strap having a first end, a second end, wherein the two ends are attached by means of a hook and loop fastener, an inner surface and an outer surface, wherein the LED assembly is attached to the inner surface of said strap at a location that interfaces with the selected section of flesh, and wherein the ECU is located on the outer suffice of said strap, wherein when said LED assembly is connected to said PCB and the FID is enabled by placing said power switch in the ON position, the flesh interfacing with said LED assembly will illuminate in accordance with the program that is stored in said light display card.

4. The FID as specified in claim 3 wherein said light display card is designed to provide an LED lighting sequence that is constant, blinks or moves sequentially in either a right direction or a left direction.

5. The FID as specified in claim 4 wherein said light display card slot is surrounded by a finger gripping indentation that allows the card to be easily grasped.

6. The FID as specified in claim 3 wherein said electrical power switch is configured as a slide switch.

7. The FID as specified in claim 3 wherein said means for attaching the fixed cover and the lower enclosure cover to said enclosure comprises a mechanical means.

8. The FID as specified in claim 3 wherein said FID control circuit is comprised of a microcontroller.

9. The FID as specified in claim 3 wherein said battery is comprised of a rechargeable battery.

10. The FID as specified in claim 3 wherein said PCB further comprises a remote control receiver that is connected to control the operation of said FID, wherein said receiver is enabled by a remotely controlled transmitter.

11. The FID as specified in claim 3 wherein said LEDs are comprised of super-bright LEDs that can be selected to produce a red, white, blue, yellow or green color as well as ultraviolet and infrared.

12. The FID as specified in claim 3 further comprising a light-leak and thermal gasket that is placed over the sides of the LEDs to prevent the emission of sidelight and to insulate the flesh from the heat produced from the LEDs.

13. The FID as specified in claim 3 wherein said flesh attachment assembly is comprised of a brassiere comprising a right cup and a left cup, wherein each cup has an upper edge, a lower edge, an inner edge, an outer edge and an inner surface, wherein the two cups are joined at their inner edges by a center section, wherein the outer edge of each cup has attached a body attachment strap, wherein each strap has ends that are placed around the body and that are secured thereto by an attachment means, wherein an LED assembly is attached by an attachment means to the inner surface and along the lower edge of each cup, wherein said ECU, which controls the operation of said LED assembly, is attached to either the center section of said brassiere or to an outer surface of one of the brassiere's body attachment straps, wherein when said FID is enabled by placing said power switch in an ON position, the flesh that interfaces with said LED assembly will illuminate in accordance with the light sequence that is stored in said light display card.

14. The FID as specified in claim 3 wherein said enclosure and said LED assembly are easily removed from the attached garment when the garment is to be laundered.

* * * * *